United States Patent [19]
Wertlake et al.

[11] 3,938,366
[45] Feb. 17, 1976

[54] AEROSOL ANALYZER

[75] Inventors: Paul Terence Wertlake, Los Angeles, Calif.; James Steele Harrison, Ringwood, N.J.

[73] Assignee: Applied Bioscience, Fairfield, N.J.

[22] Filed: Oct. 29, 1974

[21] Appl. No.: 518,229

[52] U.S. Cl. .................................. 73/28; 55/445
[51] Int. Cl.² ................................. G01N 15/06
[58] Field of Search ............ 73/28, 432 PS; 55/445, 55/446, 270

[56] References Cited
UNITED STATES PATENTS

| | | | |
|---|---|---|---|
| 2,538,116 | 1/1951 | May | 73/28 |
| 3,001,914 | 9/1961 | Andersen | 73/28 |
| 3,482,432 | 12/1969 | Mammarella | 73/28 |
| 3,693,457 | 9/1972 | Pilat | 73/432 |
| 3,795,135 | 3/1974 | Andersen | 73/28 |

*Primary Examiner*—Herbert Goldstein

[57] ABSTRACT

An apparatus for separating particles from a fluid comprising a housing, means for flowing a fluid through said housing, a plurality of parallel perforated plates supported in said housing spaced from one another in the direction of fluid flow, the plates being effective to accelerate the fluid as it passes through each plate, and a sample-holder immediately downstream of each perforated plate, the fluid flowing through each said plate onto its associated sample-holder and thence around the sample-holder to the next downstream plate, the inner wall of the housing being spaced from the path of fluid flow at least sufficient to substantially avoid contact with fluid flowing along the path.

6 Claims, 6 Drawing Figures

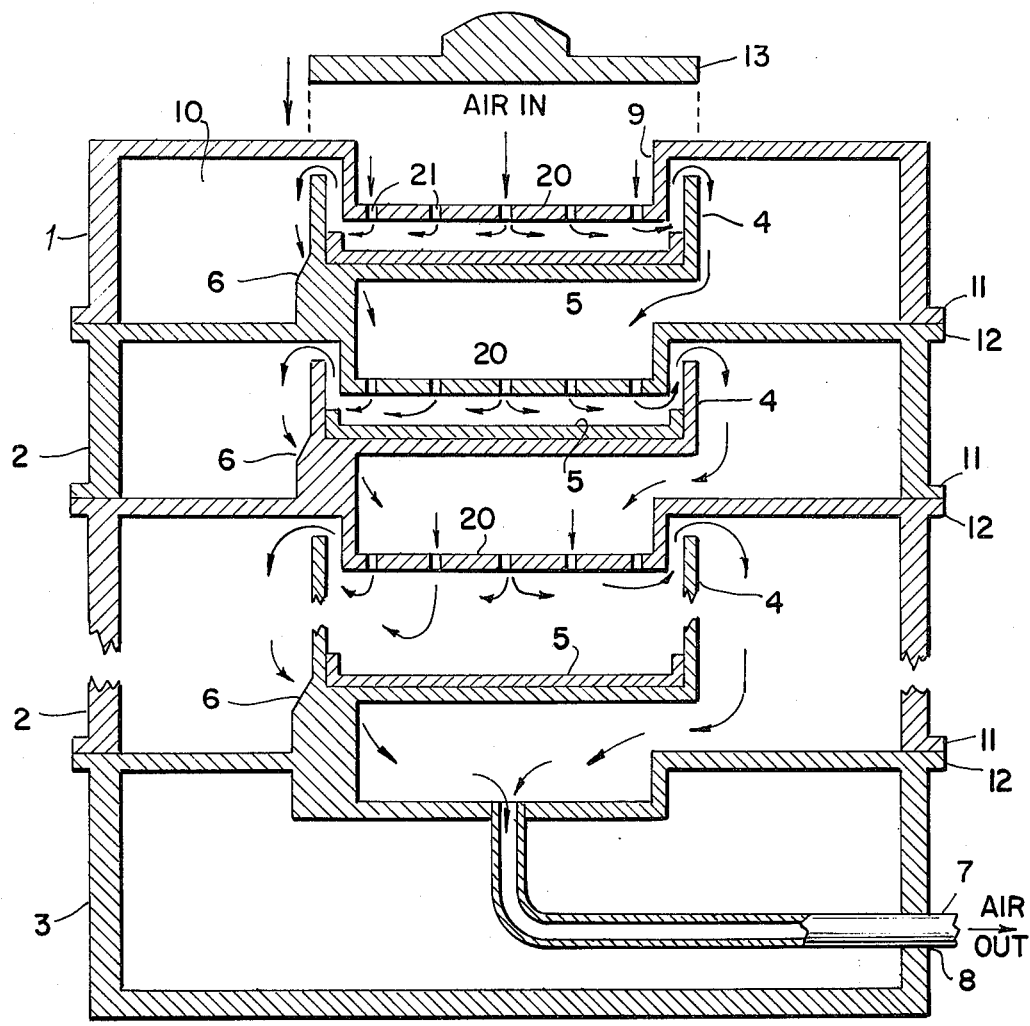
FIG.1
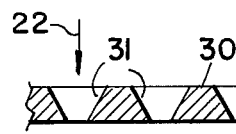
FIG.2
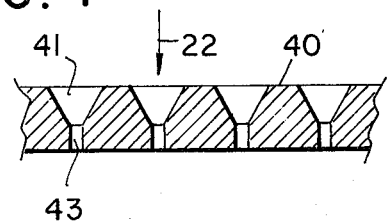
FIG.4
FIG.5
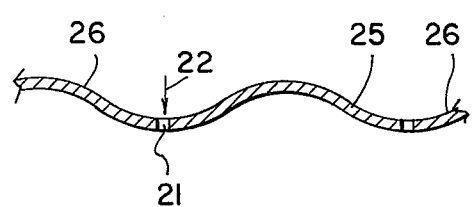
FIG.3

AEROSOL ANALYZER

The present invention relates to a method and apparatus for counting particles carried by a fluid.

In particular, the present invention relates to a method and apparatus for counting and classifying particles in air or a liquid.

There has been proposed in the prior art, a method and apparatus for counting and classifying particles in a gas, such as U.S. Pat. No. 3,001,914, issued Sept. 26, 1961 to Ariel A. Anderson. Such prior art devices cause a flow of gas through the device generally longitudinally of the device. Often, the flow of air wanders and contacts the internal walls of the device. This causes deposition of particles on the walls and gives rese to a false count.

It is an object of the present invention to provide improved apparatus capable of obtaining the utmost accuracy.

It is another object of the invention to provide a method and apparatus that is capable of economic manufacture.

These and other objects are accomplished by the present invention which provides an improved apparatus for separating particles from a fluid, comprising a housing, means for flowing a fluid through said housing, a plurality of parallel perforated plates supported in said housing spaced from one another in the direction of fluid flow, fluid accelerating means associated with each plate to accelerate said fluid as it passes through each said plate, sample-holding means immediately downstream of each perforated plate, conduit means for establishing a path of fluid flow through each said plate onto its associated sample-holding means and thence around sample-holding means to the next downstream plate, said inner wall of said housing being spaced from said path at least sufficient to substantially avoid contact with fluid flowing along said path. By providing a path for the flow of fluid that minimizes, and preferably prevents, contact of the fluid with the internal walls of the device, there is little, if any, deposition of material on these walls. Hence a more accurate count is obtained.

In another embodiment of the invention, venturi means are provided in the perforated plates such that the fluid flowing through the plates is accelerated to a higher velocity thereby to give better separation of particles from the fluid.

In another embodiment of the invention, the perforations have the same diameter from plate to plate, but there are fewer perforations per plate from plate to plate in the direction of fluid flow, thereby to accelerate the fluid as it flows through the device. If desired, the use of the venturi means may be combined with this embodiment of the invention.

This apparatus of the present invention is illustrated in terms of a preferred embodiment by the accompanying drawing, in which:

FIG. 1 is a longitudinal sectional view of the apparatus of the invention;

FIGS. 2, 3, 4 and 5 are fragmentary enlarged sectional views of modifications of the invention.

Figure 6:
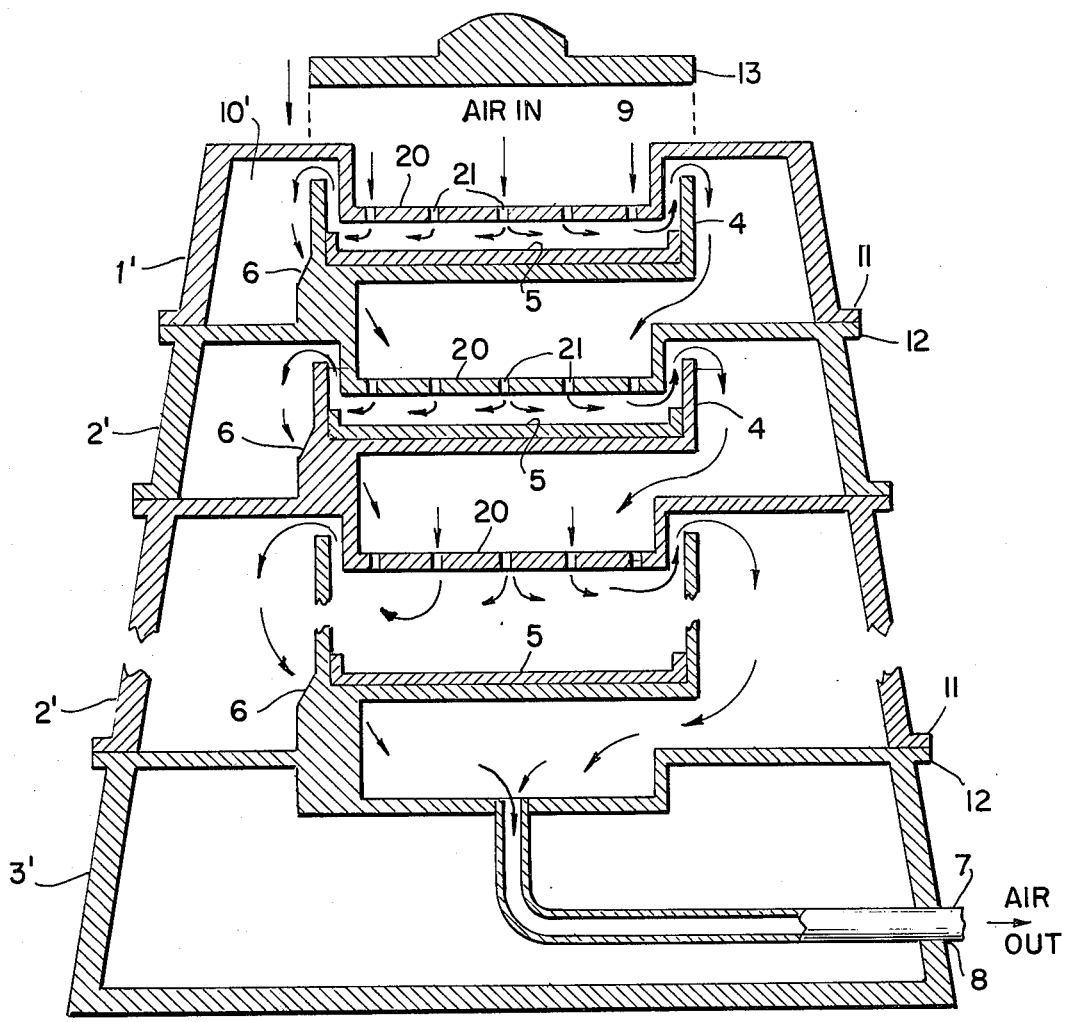
FIG. 6 is a longitudinal sectional view of another modification of the invention.

In the drawings, the filter of the invention is shown as comprising a cylindrical top stage 1, one or more intermediate cylindrical stages 2 (of which three are shown in the drawing), and a bottom cylindrical stage 3, the stages being nested together. The top stage 1 and each intermediate stage 2 has a perforated central plate 20 having perforations 21 extending radially outwardly from the center thereof to the edge. The distribution of the perforations 21 on plates 20 is not critical. Generally, the perforations will be symmetrically disposed about the center of the plate since this will encourage straight line flow of air through the plates.

Beneath each plate 20 is a cup 4, which holds a dish 5. Cups 4 are supported by a plurality of shoulders 6 disposed around the top edge of stages 2 and 3.

The stages 1, 2 and 3 may be held together by any suitable means, such as clips or the like (not shown), but a preferred embodiment of the invention is shown in FIG. 1, wherein the stages 1, 2 and 3 are sealed together by means of sealing together flanges 11 and 12. A cover 13 is frangibly sealed to the top stage 1 to cover air inlet 9 and thus keep plate 1a free from contamination. FIG. 1 shows cover 13 removed from the unit.

Each of the perforated plates 20 has the same size perforations therein, but the total number of perforations per plate decreases from the uppermost plate 20 to the lowermost plate 20. The precise number of perforations per plate will be determined by the particular separation to be effected, but is independent of the thickness of the plate 20. for example, a For unit having two stages 2 will operate satisfactorily with 200 perforations of 0.020 inches for the top plate 20, 100 perforations in the middle plate 20, 50 perforations in the bottom plate 20, each of the plates 20 being three inches in diameter. In general, the lowermost plate 20 will have from 10 to 30 per cent of the perforations of the uppermost plate, with the intermediate plates being perforated in such a manner as to provide relatively equal steps between the top and bottom plates. However, this is not essential, and the plates 20 can be perforated in such a manner that either the upper or lower plates can carry more or less perforations than would provide equal steps from plate to plate.

A suction tube 7 extending from an aperture 8 in bottom stage 3 is connected to a source of suction (not shown) and when suction is applied, air will enter through air inlet 9 and will pass through perforations 21 of the top plate 20 and will strike dish 5 immediately below. The air will then flow through stages 2 to stage 3, in the direction of the arrows. It is a feature of the invention that the inlet 9 is the same size as top plate 20, to insure that the air passes through all of perforations 21 of the first stage while minimizing, if not entirely eliminating, contact of air with the side wall of inlet 9 transverse to the direction of flow of air. An air inlet smaller than plate 20 would create flow of air over plate 20 transverse to the main flow of air.

In order further to avoid contact of the air with the walls of the unit, the cups 4 are spaced from the outermost wall of stages 1 and 2 so that a large annular air chamber 10 is formed. Chamber 10 is large enough to prevent contact of the air with the side wall of stages 1 and 2, and preferably is large enough as to provide a stagnant, toroidal air cushion between the side wall of stages 1 and 2 and the air flowing through the unit. As may be seen from FIG. 1, the flow of air shown by the arrows is spaced sufficiently far from the inner walls of stages 1 and 2, and also stage 3, to avoid contact of the inner walls with the air. For example, for a unit with cups 4 of 3 inches in diameter and employing one stage 2, the side walls of stages 1 and 2 will be spaced from the cups 4 at least about ½ inch, and preferably ¾ to 1 inch. Since the velocity of the air increases as it flows through the unit, the spacing between the cups 4 and the inner walls must either increase in the direction of air flow or, as shown in FIG. 1, the spacing can be uniform and based on the widest spacing required for the last cup downstream.

In a preferred embodiment of the invention shown in FIG. 6, the walls of stages 1′, 2′ and 3′ diverge in the direction of air flow, e.g. to provide frustoconical walls, to insure that a "dead air" space is maintained between the inner walls and the flowing gas.

As the air passes through the unit from stage 1, through stages 2, to stage 3, the velocity of the air increases from stage-to-stage due to the fact that each successive downstream stage has fewer perforations in its perforated plate 20 than the preceding upstream plate. Accordingly, the particles in the air will reach a velocity corresponding to that of the air and the largest particles will be projected down to the surface of the top dish 5. Smaller particles, whose mass is less, do not reach the surface of the top dish 5, but are carried around this dish to pass through the uppermost second stages 2. Due to the smaller number of perforations, the air velocity will be increased when it passes through the uppermost plate 20 with the result that another group of particles will strike the dish in the second stage. This process continues with progressively fewer perforations and progressively increasing air velocity at each stage, with the result that more and more of the particles are removed as the air approaches the exit of the apparatus. By choosing the proper number of perforations the the proper air rate, it is possible to remove all particles on the various stages.

When the desired air sample has been aspirated, the unit is disassembled by breaking the seal between flanges 11 and 12 and the respective dishes are removed for determination of the particles thereon. Where the particles are viable, such as bacteria or other microorganisms, the dishes 5 can be Petri dishes carrying a nutrient medium suitable to grow a viable particle. In this way, the particles become visible as colonies. However, the invention is fully operable to separate any particles, such as dust, from air or other gas.

Stages 1, 2 and 3 and cups 4 are readily made by vacuum forming of plastic. In such cases, plates 20 will be quite thin, and perforations 21 will be essentially of uniform diameter as shown in FIG. 2. A modified plate 25 is shown in FIG. 3 wherein plate 25 is vacuum formed from thin plastic with the formation of dimples 26. The walls of dimples 26 converge in the direction of air flow and act as a venturi. Where other molding techniques are used, plates 20 can conveniently be made with a thicker section, such as the modified plates 30 (FIG. 4) and 40 (FIG. 5). In FIG. 4, the perforations are provided with converging walls 31 in the direction of air flow 21. In FIG. 5, the perforations have an upstream converging section 41 and a downstream section 42 of constant diameter to simulate a venturi. In the case of FIGS. 3–5, the air will be accelerated as it passes through plates 25, 30 and 40, thus enhancing the aceleration effect of the unit. Of course, any of the plates 20, 25, 30 or 40 can be used in the embodiments of FIGS. 1 or 6.

While the present invention has been illustrated herein in terms of particles entrained in air, it is operable with respect to separation of any particles from any fluid, whether gas or liquid. Thus, particles entrained in water or other liquid can be separated and counted. Moreover, by proper choice of reactant in cups 4, the material separated from the fluid can be caused to react with the reactant to provide a reaction product that can be collected as such as a useful product or merely used for analysis by any one of a number of suitable techniques. For example, the particles can be virus particles that are bound to a gamma globulin material on cup 4, and radio-immune assay can be used to determine the number of virus particles collected on each cup. Alternatively, the fluid can contain trace quantities of a valuable material, which is caused to react with a reactant in cup 4 to provide a valuable product. In a further embodiment, the cups 4 are covered with a permselective membrane (not shown) and the cups 4 contain a reactant. A liquid is flowed through the device and the membranes continuously transfer only a desired component of the liquid for continuous reaction with the reactant.

What is claimed is:

1. Apparatus for separating particles from a fluid, comprising a housing, means for flowing a fluid through said housing, a plurality of parallel perforated plates supported in said housing spaced from one another in the direction of fluid flow, the perforations of each plate being of the same size with the number of perforations per plate being fewer in the direction of fluid flow, sample-holding means immediately downstream of each perforated plate, and conduit means for establishing a path of fluid flow through each said plate onto its associated sample-holding means and thence around said sample-holding means to the next downstream plate, said inner wall of said housing being spaced from said path at least sufficient to substantially avoid contact with fluid flowing along said path.

2. Apparatus according to claim 1, wherein at least a portion of the perforations have at least a portion of their walls converging in the direction of fluid flow.

3. Apparatus according to claim 2, wherein said converging perforations are conical or frustoconical.

4. Apparatus according to claim 1, wherein each plate and its associated sample-holding means forms a sub-unit, and the sub-units are connected together by fluid-tight seals.

5. Apparatus according to claim 1, wherein said housing has air inlet means opening directly into the plate furthest upstream, said air inlet means having the same cross-sectional area as said furthest upstream plate.

6. Apparatus according to claim 1, wherein said inner wall is of frustoconical shape and diverges in the direction of fluid flow.

* * * * *